United States Patent
Dellinger et al.

(10) Patent No.: US 7,855,281 B2
(45) Date of Patent: *Dec. 21, 2010

(54) CLEAVABLE THIOCARBONATE LINKERS FOR POLYNUCLEOTIDE SYNTHESIS

(75) Inventors: Douglas J Dellinger, Boulder, CO (US); Zoltan Timar, Boulder, CO (US); Joel Myerson, Berkeley, CA (US); Geraldine Dellinger, Boulder, CO (US); Marvin Caruthers, Boulder, CO (US)

(73) Assignees: Agilent Technologies, Inc., Santa Clara, CA (US); The Regents of the University of Colorado, Boulder, CO (US)

( * ) Notice: Subject to any disclaimer, the term of this patent is extended or adjusted under 35 U.S.C. 154(b) by 185 days.

This patent is subject to a terminal disclaimer.

(21) Appl. No.: 11/389,326

(22) Filed: Mar. 23, 2006

(65) Prior Publication Data

US 2007/0224602 A1    Sep. 27, 2007

(51) Int. Cl.
*C07H 19/00*    (2006.01)
*C07H 21/00*    (2006.01)

(52) U.S. Cl. ................................. 536/22.1; 536/25.3
(58) Field of Classification Search .................... None
See application file for complete search history.

(56) References Cited

U.S. PATENT DOCUMENTS

| | | | | | |
|---|---|---|---|---|---|
| 5,859,233 | A | * | 1/1999 | Hirschbein et al. | 536/26.1 |
| 6,222,030 | B1 | * | 4/2001 | Dellinger et al. | 536/25.3 |
| 6,673,918 | B2 | * | 1/2004 | Bellon et al. | 536/25.31 |
| 2005/0048497 | A1 | * | 3/2005 | Dellinger et al. | 435/6 |
| 2005/0136477 | A1 | * | 6/2005 | Akhavan-Tafti | 435/6 |
| 2007/0100136 | A1 | * | 5/2007 | Dellinger et al. | 536/23.1 |

OTHER PUBLICATIONS

McIsaac et al., The Nucleophilic Reactivity of Peroxy Anions, J. Org. Chem., vol. 37, No. 7, 1972 pp. 1037-1041.*

* cited by examiner

*Primary Examiner*—Mark Staples (57) ABSTRACT

In various embodiments of the invention, novel compositions having a polynucleotide bound to a substrate via a cleavable linker are provided, and methods of cleaving a polynucleotide from a substrate are provided.

14 Claims, 1 Drawing Sheet

Fig._1

CLEAVABLE THIOCARBONATE LINKERS FOR POLYNUCLEOTIDE SYNTHESIS

RELATED APPLICATIONS

Related subject matter is disclosed in U.S. patent application filed by Dellinger et al. entitled "Monomer Compositions for the Synthesis of Polynucleotides, Methods of Synthesis, and Methods of Deprotection" (Ser. No. 11/387,388); U.S. patent application filed by Dellinger et al. entitled "Monomer Compositions for the Synthesis of Polynucleotides, Methods of Synthesis, and Methods of Deprotection" (Ser. No. 11/388, 112); U.S. patent application filed by Dellinger et al. entitled "Solutions, Methods, and Processes for Deprotection of Polynucleotides" (Ser. No. 11/387,269); U.S. patent application filed by Dellinger et al. entitled "Use of Mildly Basic Solutions of Peroxyanions for the Post-Synthesis Deprotection of RNA Molecules and Novel Monomer Compositions for the Synthesis of RNA" (Ser. No. 60/785,130); U.S. patent application filed by Dellinger et al. entitled "Cleavable Linkers for Polynucleotides" (Ser. No. 11/389,388); U.S. patent application filed by Dellinger et al. entitled "Phosphorus Protecting Groups" (Ser. No. 11/388,339); all above-mentioned patent applications filed on the same day as the present application. Related subject matter is also disclosed in U.S. patent application filed on Oct. 31, 2005 by Dellinger et al. entitled "Methods for Deprotecting Polynucleotides" having Ser. No. 60/731,723.

FIELD OF THE INVENTION

The invention relates generally to nucleic acid chemistry. More particularly, the invention relates to providing a cleavable linker for release of polynucleotides, e.g. from a substrate. The invention is useful in the manufacture of reagents and devices used in the fields of biochemistry, molecular biology and pharmacology, and in medical diagnostic and screening technologies, as well as other uses.

BACKGROUND OF THE INVENTION

Solid phase chemical synthesis of DNA fragments is routinely performed using protected nucleoside phosphoramidites. Beaucage et al. (1981) Tetrahedron Lett. 22:1859. In this approach, the 3'-hydroxyl group of an initial 5'-protected nucleoside is first covalently attached to the polymer support. Pless et al. (1975) Nucleic Acids Res. 2:773. Synthesis of the oligonucleotide then proceeds by deprotection of the 5'-hydroxyl group of the attached nucleoside, followed by coupling of an incoming nucleoside-3'-phosphoramidite to the deprotected hydroxyl group. Matteucci et al. (1981) J. Am. Chem. Soc. 103:3185. The resulting phosphite triester is finally oxidized to a phosphotriester to complete one round of the synthesis cycle. Letsinger et al. (1976) J. Am. Chem. Soc. 98:3655. The steps of deprotection, coupling and oxidation are repeated until an oligonucleotide of the desired length and sequence is obtained. Optionally, after the coupling step, the product may be treated with a capping agent designed to esterify failure sequences and cleave phosphite reaction products on the heterocyclic bases.

Solid phase polynucleotide synthesis results in a polynucleotide bound upon a solid support. Typically, an additional step releases the polynucleotide from the solid support after the polynucleotide strand has been synthesized. This release step yields the polynucleotide in solution, which may then be separated from the solid support, e.g. by filtration or other suitable methods. The release step is dependent upon having a support that is functionalized with a releasable moiety that, while inert under the conditions used in the synthesis cycle, provides for the release of the synthesized polynucleotide under conditions conducive for doing so.

The concept of a "safety catch linker" has been exploited widely. These linkers were originally developed by Kenner for peptide synthesis (Kenner et al. (1971) J. Chem. Soc. Chem. Commun. pp 636-37). They were designed to be cleaved in a two-stage process, where the first step involves activation of a functional group on the linker, and the second step involves the actual cleavage of the linker. After the functional group has been activated the cleavage step is more facile than it would have been prior to activation. Kenner's safety catch linker is stable to both acidic and basic conditions until the nitrogen is alkylated (activation), then cleaved by nucleophilic attack, for example with hydroxide or nucleophilic amine.

Another example of a safety catch linker, developed by Marshall and Liener (Marshall, D. L.; Liener, I. E., J. Org. Chem., 1970, 35, 867-868), exploits the activation of a sulfide by oxidation to the sulfone. After activation with hydrogen peroxide, the linker is cleaved with an amine nucleophile.

The concept of "safety catch linkers" has been further explored with a variety of type of activation methods prior to cleavage of the linker: most activation steps are performed through alkylation, oxidation, or neighboring group effects. However, these previously described processes are performed as two independent steps often requiring several independent reagents.

While there are examples of cleavable linkers in the literature, there remains a need for novel cleavable linkers for polynucleotides, e.g. polynucleotides bound to a substrate.

SUMMARY OF THE INVENTION

In various embodiments of the invention, novel compositions having a polynucleotide bound to a substrate via a cleavable linker are provided, and methods of cleaving a polynucleotide from a substrate are provided. The cleavable linkers are cleavable under conditions that include contact with an α-effect nucleophile.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the materials and methods particularly pointed out in the appended claims.

BRIEF DESCRIPTION OF THE DRAWINGS

These and other features of the invention will be understood from the description of representative embodiments of the method herein and the disclosure of illustrative materials for carrying out the method, taken together with the Figures, wherein.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "a substituent", as in a compound substituted with "a substituent", includes the possibility of substitution with more than one substituent, wherein the substituents may be the same or different. In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleobase" references the heterocyclic base of a nucleoside or nucleotide. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected.

As used herein, polynucleotides include single or multiple stranded configurations, where one or more of the strands may or may not be completely aligned with another. The terms "polynucleotide" and "oligonucleotide" are generic to polydeoxynucleotides (containing 2-deoxy-D-ribose), to polyribonucleotides (containing D-ribose), to any other type of polynucleotide having nucleotide subunits that are N-glycosides of a purine or pyrimidine base, and to other polymers in which the conventional backbone has been replaced with a non-naturally occurring or synthetic backbone or in which one or more of the conventional bases has been replaced with a non-naturally occurring or synthetic base. An "oligonucleotide" generally refers to a nucleotide multimer of about 2 to 200 nucleotides in length, while a "polynucleotide" includes a nucleotide multimer having at least two nucleotides and up to several thousand (e.g. 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to eight carbon atoms and further having additional groups, such as one or more linkages selected from ether-, thio-, amino-, phospho-, keto-, ester- and amido-, and/or being substituted with one or more groups including lower alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more typically selected from the group consisting of lower alkyl, modified lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl thio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

The term "halo" or "halogen" is used in its conventional sense to refer to a chloro, bromo, fluoro or iodo substituent.

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

By "protecting group" as used herein is meant a species which prevents a portion of a molecule from undergoing a specific chemical reaction, but which is removable from the molecule following completion of that reaction, as taught for example in Greene, et al., "Protective Groups in Organic Synthesis," John Wiley and Sons, Second Edition, 1991. A "peroxyanion-labile linking group" is a linking group that releases a linked group when contacted with a solution containing peroxyanions. Similarly, a "peroxyanion-labile protecting group" is a protecting group that is removed from the corresponding protected group when contacted with a solution containing peroxyanions. As used herein, "2'-O protecting groups" or "2'-hydroxyl protecting groups" are protecting groups which protect the 2'-hydroxyl groups of the polynucleotide (e.g. bound to the 2'-O). As used herein, "phosphorus protecting group" (sometimes referenced as "phosphate protecting group") references a protecting group which protects a phosphorus group (e.g. is bound to a phosphorus group wherein the phosphorus group is attached to a sugar moiety of, e.g. a nucleotide, a nucleoside phosphoramidite, a polynucleotide intermediate, or a polynucleotide). As used herein, "cleaving", "cleavage", "deprotecting", "releasing", or like terms when used in reference to a protecting group refers to breaking a bond via which the protecting group is bound to the protected group, resulting in the cleaved protecting group and the deprotected moiety (the moiety that was the protected group when bound to the protecting group).

The term "electron withdrawing" denotes the tendency of a substituent to attract valence electrons of the molecule of which it is a part, i.e., an electron-withdrawing substituent is electronegative with respect to neighboring atoms. A quantification of the level of electron-withdrawing capability is given by the Hammett sigma constant. This well known constant is described in many references, for instance, March, Advanced Organic Chemistry 251-59, McGraw Hill Book Company, New York, (1977). Exemplary electron-withdrawing groups include nitro, acyl, formyl, sulfonyl, trifluoromethyl, cyano, chloride, and the like.

The term "electron-donating" refers to the tendency of a substituent to repel valence electrons from neighboring atoms, i.e., the substituent is less electronegative with respect to neighboring atoms. Exemplary electron-donating groups include amino, methoxy, alkyl (including alkyl having a linear or branched structure, alkyl having one to eight carbons), cycloalkyl (including cycloalkyl having four to nine carbons), and the like.

The term "alpha effect," as in an "alpha effect nucleophile" in a deprotection/oxidation agent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm. 171; Buncel et al. (1982) J. Am. Chem. Soc. 104:4896; Edwards et al. (1962) J. Am. Chem. Soc. 84:16; Evanseck et al. (1987) J. Am. Chem Soc. 109:2349. The magnitude of the alpha effect is dependent upon the electrophile which is paired with the specific nucleophile. McIsaac, Jr. et al. (1972), J. Org. Chem. 37:1037. Peroxy anions are example of nucleophiles which exhibit strong alpha effects.

"Moiety" and "group" are used interchangeably herein to refer to a portion of a molecule, typically having a particular functional or structural feature, e.g. a linking group (a portion of a molecule connecting two other portions of the molecule), or an ethyl moiety (a portion of a molecule with a structure closely related to ethane).

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phosphate (—PO$_4$H—), ester (—O—C(O)—).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, amino, imino, amido, alkylamino, arylamino, alkoxy, aryloxy, thio, alkylthio, arylthio, alkyl; aryl, thioalkyl, hydroxyl, mercapto, halo, cyano, nitro, nitroso, azido, carboxy, sulfide, sulfonyl, sulfoxy, phosphoryl, silyl, silyloxy, and boronyl optionally substituted on one or more available carbon atoms with a nonhydrocarbyl substituent such as cyano, nitro, halogen, hydroxyl, sulfonic acid, sulfate, phosphonic acid, phosphate, or phosphonate or the like. Any substituents are typically chosen so as not to substantially adversely affect reaction yield (for example, not lower it by more than 20% (or 10%, or 5% or 1%) of the yield otherwise obtained without a particular substituent or substituent combination).

As used herein, "dissociation constant", e.g. an acid dissociation constant, has its conventional definition as used in the chemical arts and references a characteristic property of a molecule having a tendency to lose a hydrogen ion. The value of a dissociation constant mentioned herein is typically expressed as a negative $\log_{10}$ value, i.e. a pKa (for an acid dissociation constant).

Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

We have now developed a set of conditions using peroxyanions that are effective at cleaving certain types of cleavable linkers in a single step using a single reagent. This allows for more efficient chemical procedures as well as increased flexibility due to the mildness of the cleavage conditions. Thus, in various embodiments of the invention, novel compositions comprising a polynucleotide bound to a substrate via a cleavable linker are provided, and methods of cleaving a polynucleotide from a substrate are provided.

Accordingly, in certain embodiments of the present invention, a composition is provided having a polynucleotide bound to a substrate via a cleavable linker.

In typical embodiments, the cleavable linker has the structure (I):

wherein:
Lnk is a linking group;
Sub denotes the site at which the substrate is attached to the cleavable linker; and
RPN denotes the site at which the polynucleotide is attached to the cleavable linker.

The polynucleotide attached to the substrate via the cleavable linker may be any polynucleotide, for example DNA, RNA, a polynucleotide analog, a modified polynucleotide, a polynucleotide having protecting groups (e.g. protecting groups bound to the amine groups of nucleobases, protecting groups bound to the phosphate groups of the polynucleotide, protecting groups which protect hydroxyl groups of the polynucleotide (e.g. bound to the 2'-O), or other protecting groups). The polynucleotide may be synthesized in situ (e.g. synthesized one nucleotide at a time using polynucleotide synthesis schemes well known in the art) or may be separately synthesized and then attached to the substrate via the cleavable linker. For example, a modified cleavable linker moiety is bound to the substrate, wherein the modified cleavable linker moiety has a protected nucleotide moiety bound to a cleavable linker moiety as described herein. The protected nucleotide moiety is then deprotected, and the deprotected nucleotide moiety serves as a site to either start in situ synthesis of a full length polynucleotide or as a site for attachment of an already synthesized polynucleotide. Other methods of providing the polynucleotide attached to the substrate via the cleavable linker are possible and may be employed in accordance with the present invention. The polynucleotide may generally be attached to the cleavable linker via any available site of the polynucleotide, e.g. at the 2'-O, the 3'-O, the 5'-O, an amino group of a nucleobase, or any other site, given that the available site provides a resulting structure that is cleavable upon contacting the polynucleotide-bound substrate with the α-effect nucleophile. Typically, the polynucleotide is attached to the cleavable linker at the 2'-O or the 3'-O, less typically at the 5'-O or at an amino group of a nucleobase.

In particular embodiments, the polynucleotide has a 2'-hydroxyl protecting group and at least one additional protecting group selected from a nucleobase protecting group and a phosphorus protecting group, wherein said 2'-hydroxyl protecting group is characterized as stable under conditions which include an α-effect nucleophile; and wherein said at least one additional protecting group is characterized as labile under conditions which include an α-effect nucleophile.

In particular embodiments, the polynucleotide has a 2'-hydroxyl protecting group, a phosphorus protecting group, and a nucleobase protecting group, wherein the 2'-hydroxyl protecting group and phosphate protecting group are characterized as stable under conditions which include an α-effect nucleophile; and wherein the nucleobase protecting group is characterized as labile under conditions which include an α-effect nucleophile.

Referring to structure (I), the linking group -Lnk- is selected from (1) a linking group linking the substrate and the cleavable linker; or (2) a covalent bond between the substrate and the cleavable linker (e.g. the cleavable linker is directly bound to the substrate). In particular embodiments, the linking group -Lnk- may be any appropriate linking group via which the substrate is attached to the cleavable linker. The linking group -Lnk- is typically selected from (1) a lower alkyl group; (2) a modified lower alkyl group in which one or more linkages selected from ether-, thio-, amino-, oxo-, ester-, and amido- is present; (3) a modified lower alkyl substituted with one or more groups including lower alkyl; aryl, aralkyl, alkoxyl, thioalkyl, hydroxyl, amino, amido, sulfonyl, halo; or (4) a modified lower alkyl substituted with one or more groups including lower alkyl; alkoxyl, thioalkyl, hydroxyl, amino, amido, sulfonyl, halo, and in which one or more linkages selected from ether-, thio-, amino-, oxo-, ester-, and amido- is present. The linking group -Lnk- may be bonded to the substrate at any position of the linking group -Lnk- available to bind to the substrate. Similarly, the linking group -Lnk- may be bonded to the adjacent cleavable linker at any position of the linking group -Lnk- available to bind to the adjacent cleavable linker. In certain embodiments, the linking group -Lnk- is a single methylene group, e.g. —CH2-, or may be an alkyl group or modified alkyl group up to about 24 carbons long (and which may be straight-chain or branched-chain). In certain such embodiments, one or more linkages selected from ether-, oxo-, thio-, and amino- is present in the straight-or branched chain modified alkyl group. In an embodiment, the linking group -Lnk- comprises optionally substituted ethoxy, propoxy, or butoxy groups (i.e. may include the structure —{(CH2)m-O}n-, wherein m is a integer selected from 2, 3, 4, and n is a integer selected from 1, 2, 3, 4, 5, 6). In an embodiment, the linking group -Lnk- has the structure —(CH2)m-Lkg-(CH2)n-, wherein m and n are integers independently selected from the range of 1 to about 12, e.g. from the range of 2 to about 8, and Lkg is a linkage selected from ether-, thio-, amino-, oxo-, ester-, and amido-.

In particular embodiments, the linking group -Lnk- has a first terminal site and a second terminal site. In such embodiments, the linking group -Lnk- is bound to the substrate at the first terminal site, and the linking group -Lnk- is bound to the cleavable linker at the second terminal site. The first and second terminal sites will depend on the design of the linking group taking into consideration, for example, the method used to attach the cleavable linker to the substrate.

The cleavable linker may be attached to a suitable substrate that may have a variety of forms and compositions. The substrate may derive from naturally occurring materials, naturally occurring materials that have been synthetically modified, or synthetic materials. Examples of suitable support materials include, but are not limited to, nitrocellulose, glasses, silicas, teflons, and metals (e.g., gold, platinum, and the like). Suitable materials also include polymeric materials, including plastics (for example, polytetrafluoroethylene, polypropylene, polystyrene, polycarbonate, and blends thereof, and the like), polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, and the like.

The cleavable linker may be bound directly to the substrate (e.g. to the surface of the substrate, e.g. to a functional group on the surface) or indirectly bound to the substrate, e.g. via one or more intermediate moieties (e.g. linking groups) and/or surface modification layer on the substrate. The nature of the site on the substrate to which the cleavable linker is attached (e.g. directly or via a linking group) is not essential to the present invention, as any known coupling chemistry compatible with the sensor substrate (i.e. which doesn't result in significant degradation of the sensor substrate) may be used to couple to the cleavable linker. As such, various strategies of coupling the cleavable linker to substrates using functional groups on the substrates are known in the art and may be employed advantageously in the disclosed methods. Typical strategies require a complementary reactive group on the cleavable linker or are selected based on moieties already present on the cleavable linker (e.g. amino groups, hydroxyl groups, or other functional groups), for example an active group on the substrate that is capable of reacting with a corresponding reactive group attached to the linker to result in the linker covalently bound to the substrate.

Accordingly, in certain embodiments of the present invention, a method is provided wherein the method includes: contacting a polynucleotide bound to a substrate via a cleavable linker with a solution comprising an $\alpha$-effect nucleophile to result in cleavage of the polynucleotide from the substrate; wherein the cleavable linker has the structure (I), as described above.

As mentioned above, embodiments of the present disclosure include methods for cleaving a polynucleotide from a substrate, wherein the polynucleotide is bound to a cleavable linker such as those described herein. In particular embodiments, the method includes contacting the polynucleotide bound to the substrate via the cleavable linker with a solution of an $\alpha$-effect nucleophile (e.g., a peroxyanion solution), where the $\alpha$-effect nucleophile has a pKa of about 4 to 13. In addition, the solution is at a pH of about 6 to 11.

In particular embodiments, a polynucleotide bound to a substrate via a cleavable linker is contacted with a solution of peroxyanions to result in cleavage of the polynucleotide from the substrate, wherein the peroxyanions have a pKa within the range 4-12, at neutral to mildly basic pH (e.g. the pH typically is in the range from about 6 to about 11).

In typical embodiments, the conditions employed for deprotection include contacting the polynucleotide with the solution of the $\alpha$-effect nucleophile for time sufficient to result in cleavage of the phosphorus protecting group. Typical times (duration) for the cleavage reaction range from about 15 minutes to about 24 hour, although times outside this range may be used. Typically the duration of the contacting is in the range from about 30 minutes to about 16 hours, e.g. from about 45 minutes to about 12 hours, from about 1 hour to about 8 hours, or from about 1 hour to about 4 hours.

One advantage of using a neutral to mildly basic (e.g. pH in the range from about 6 to about 11) solution including an $\alpha$-effect nucleophile is that the solution including an $\alpha$-effect nucleophile is compatible with standard phosphoramidite methods for polynucleotide synthesis. Further, the polynucleotides released from the substrate by cleavage of the cleavable linker are stable and show little or no degradation for an extended period of time when stored in the solution including the $\alpha$-effect nucleophile.

In general, the solution including the $\alpha$-effect nucleophile can be a predominantly buffered aqueous solution or buffered aqueous/organic solution. Under these conditions it is convenient and cost effective to recover the released polynucleotide from the mixture of released polynucleotide and solution of $\alpha$-effect nucleophile by simple precipitation of the desired polynucleotides directly from the mixture by addition of ethanol to the mixture. Under these conditions, the polynucleotide is pelleted to the bottom of a centrifuge tube and the supernatant containing the $\alpha$-effect nucleophile removed by simply pouring off the supernatant and rinsing the pellet with fresh ethanol. The released polynucleotide is then isolated by resuspending in a typical buffer for chromatographic purification or direct usage in the biological experiment of interest. Because of the nature of most α-effect nucleophiles, removal from the desired released polynucleotide products is easy, quick, and effective using the ethanol precipitation method. Any other methods of recovering the polynucleotides may be employed, such as using Micro Bio-Spin™ chromatography columns (BioRad, Hercules, Calif.) for cleanup and purification of polynucleotides (used according to product insert instructions).

The solution including the α-effect nucleophile typically may have a pH in the range of about 4 to 11, about 5 to 11, about 6 to 11, about 7 to 11, about 8 to 11, about 4 to 10, about 5 to 10, about 6 to 10, about 7 to 10, or about 8 to 10. In particular embodiments the solution has a pH of about 7 to 10. It should also be noted that the pH is dependent, at least in part, upon the α-effect nucleophile in the solution and the protecting groups on the polynucleotide. Appropriate adjustments to the pH can be made to the solution to accommodate the α-effect nucleophile.

The α-effect nucleophiles can include, but are not limited to, peroxyanions, hydroxylamine derivatives, hydroximic acid and derivatives thereof, hydroxamic acid and derivatives thereof, carbazide and semicarbazides and derivatives thereof. The α-effect nucleophiles can include compounds such as, but not limited to, hydrogen peroxide, peracids, perboric acid salts, alkylperoxides, hydrogen peroxide salts, hydroperoxides, butylhydroperoxide, benzylhydroperoxide, phenylhydroperoxide, cumene hydroperoxide, performic acid, peracetic acid, perbenzoic acid and substituted perbenzoic acids such as chloroperbenzoic acid, perbutyric acid, tertiary-butylperoxybenzoic acid, decanediperoxoic acid, other similar compounds, and corresponding salts, and combinations thereof. Hydrogen peroxide, salts of hydrogen peroxide and mixtures of hydrogen peroxide and performic acid are especially useful. Hydrogen peroxide, whose pKa is around 11, is particularly useful in solutions above pH 9.0. Below pH 9.0 there is no significant concentration of peroxyanion to work as an effective nucleophile. Below pH 9.0 it is especially useful to use mixtures of hydrogen peroxide and peracids. These peracids can be preformed and added to the solution or they can be formed in situ by the reaction of hydrogen peroxide and the carboxylic acid or carboxylic acid salt. An example is that an equal molar mixture of hydrogen peroxide and sodium formate can be used at pH conditions below 9.0 as an effective α-effect nucleophile solution where hydrogen peroxide alone is not provide a high concentration of α-effect nucleophiles. The utility of peracids tends to be dependent upon the pKa of the acid and size of molecule: the higher the pKa of the acid the more useful as a peroxyanion solution, the larger the size of the molecule the less useful. Typically the pKa of the peracid is lower than the pH of the desired peroxyanion solution.

The α-effect nucleophiles typically used in these reactions are typically strong oxidants, therefore one should limit the concentration of the reagent in the solution in order to avoid oxidative side products where undesired. The α-effect nucleophiles are typically less than 30% weight/vol of the solution, more typically between 0.1% and 10% weight/vol of the solution and most typically 3% to 7% weight/vol of the solution. The typical 3% solution of hydrogen peroxide is about 1 molar hydrogen peroxide. A solution of between 1 molar and 2 molar hydrogen peroxide is typically useful. A typical solution of hydrogen peroxide and performic acid is an equal molar mixture of hydrogen peroxide and performic acid, both in the range of 1 to 2 molar. An example of an in situ prepared solution of performic acid is 2 molar hydrogen peroxide and 2 molar sodium formate buffered at pH 8.5.

In typical embodiments, the α-effect nucleophile is characterized as having a pKa in the range from about 4 to 13, about 4 to 12, about 4 to 11, about 5 to 13, about 5 to 12, about 5 to 11, about 6 to 13, about 6 to 12, about 6 to 11, about 7 to 13, about 7 to 12, or about 7 to 11.

It should also be noted that the dissociation constant (the pKa) is a physical constant that is characteristic of the specific α-effect nucleophile. Chemical substitution and solvent conditions can be used to raise or lower the effective dissociation constant and therefore specifically optimize the conditions under which the cleavage of the cleavable linker is performed (to result in release of the polynucleotide from the substrate, and, optionally, deprotection of groups protected by peroxyanion-labile protecting groups). Appropriate selection of the α-effect nucleophile should be made considering the other conditions of the method and the protecting groups of the polynucleotide. In addition, mixtures of carboxylic acids and hydroperoxides can be used to form salts of peracids in situ.

As an example a solution of hydrogen peroxide can be used with a solution of formic acid at pH conditions below 9.0. At pH conditions less than 9.0 hydrogen peroxide is not significantly ionized due to its ionization constant of around 11. At pH 7.0 only about 0.01% of the hydrogen peroxide is in the ionized form of the α-effect nucleophile. However, the hydrogen peroxide can react in situ with the formic acid to form performic acid in a stable equilibrium. At pH 7.0 the performic acid is significantly in the ionized form and is an active α-effect nucleophile. The advantage of such an approach is that solutions of performic acid tend to degrade rapidly and stabilizers need to be added. The equilibrium that is formed between the hydrogen peroxide solutions and the formic acid helps stabilize the performic acid such that it can be used to completely cleave the polynucleotides from the substrates prior to degrading. Performic acid is especially useful in a buffered mixture of hydrogen peroxide at pH 8.5 because the pKa of performic acid is approximately 7.1. Peracetic acid is useful at pH 8.5 but less useful than performic acid because the pKa of peracetic acid is approximately 8.2. At pH 8.5 peracetic acid is only about 50% anionic whereas at pH 8.5 performic acid is more than 90% anionic.

In general, the pKa for the hydroperoxides is about 8 to 13. The pKa for hydrogen peroxide is quoted to be about 10 to 12 depending upon the method of analysis and solvent conditions. The pKa for the alkylperoxides is about 8 to 14. The pKa for the peracids is about 3 to 9. In some embodiments in which the peroxyanion is hydroperoxide, the solution is at pH of about 9 to 11, e.g. at a pH of about 9 to about 10. In certain embodiments in which the peroxyanion is an alkylperoxide, the solution is at pH of about 8 to 11. In embodiments where the peroxyanion is a peracid, the solution is at pH of about 6 to 9. In addition, the peracid typically has a pKa of about 4 to 10.

In addition, the aqueous buffer solution usually includes a buffer, such as, but not limited to, tris(hydroxymethyl)aminomethane, aminomethylpropanol, citric acid, N,N'-Bis(2-hydroxyethyl)glycine, 2-[Bis(2-hydroxyethyl)amino]-2-(hydroxy-methyl)-1,3-propanediol, 2-(Cyclohexylamino) ethane-2-sulfonic acid, N-2-Hydroxyethyl)piperazine-N'-2-ethane sulfonic acid, N-(2-Hydroxyethyl)piperazine-N'-3-propane sulfonic acid, Morpholinoethane sulfonic acid, Morpholinopropane sulfonic acid, Piperazine-N,N'-bis(2-ethane sulfonic acid), N-Tris(hydroxymethyl)methyl-3-aminopropane sulfonic acid, N-Tris(hydroxymethyl)methyl-2-aminoethane sulfonic acid, N-Tris(hydroxymethyl) methylglycine, and combinations thereof.

One significant potential advantage for cleaving the polynucleotide from a substrate according to the present methods is that the α-effect nucleophile solution can be exploited to remove a variety of peroxyanion-labile protecting groups at the same time and under the same conditions that are used to cleave the polynucleotide from the substrate. Thus, cleavage of the polynucleotide from the substrate and deprotection of groups protected with peroxyanion-labile protecting groups may be reduced to a single step in which the cleavage and deprotection occur at essentially the same time in the same reaction mixture. These advantages become even more significant if they are used with the protecting groups described in the applications cited herein to Dellinger et al. that were filed on the same day as the present application; such protecting groups specifically provide for rapid deprotection under the oxidative, nucleophilic conditions at neutral to mildly basic pH.

Particularly contemplated is the use of the cleavable linkers described herein in conjunction with peroxyanion-labile protecting groups attached to the polynucleotide. The peroxyanion-labile protecting groups may be attached, e.g. at the 2'-position of the nucleoside sugar of the individual nucleotide subunits, at the exocyclic amine groups of the heterocyclic bases of the polynucleotide, at the imine groups of the heterocyclic bases of the polynucleotide, and/or at the phosphate groups of the backbone of the polynucleotide. In certain such embodiments, contacting the polynucleotide with solution including an α-effect nucleophile results in concurrent cleavage of the polynucleotide from the substrate and deprotection of the polynucleotide, e.g. at the 2'-position of the nucleoside sugar, at the exocyclic amine groups, at the imine groups of the heterocyclic bases, and/or at the phosphate groups.

For example, in particular embodiments a polynucleotide bound to a substrate via a cleavable linker as described herein has peroxyanion-labile protecting groups on, e.g. the exocyclic amine groups. In some such embodiments, contacting the polynucleotide with solution including an α-effect nucleophile results in concurrent cleavage of the polynucleotide from the substrate and deprotection of the exocyclic amine groups. As another example, in particular embodiments a polynucleotide bound to a substrate via a cleavable linker as described herein has peroxyanion-labile protecting groups on, e.g. the 2' position of the nucleoside sugar. In certain such embodiments, contacting the polynucleotide with a solution including an α-effect nucleophile results in concurrent cleavage of the polynucleotide from the substrate and deprotection of the 2' position of the nucleoside sugar (e.g. resulting in a deprotected 2'-hydroxyl group). In a further example, a polynucleotide bound to a substrate via a cleavable linker has peroxyanion-labile protecting groups on, e.g. the 2' position of the nucleoside sugar and the exocyclic amine groups. In certain such embodiments, contacting the polynucleotide with a solution including an α-effect nucleophile results in concurrent cleavage of the polynucleotide from the substrate and deprotection of the 2' position of the nucleoside sugar and the exocyclic amine groups.

Structure (VII) serves to illustrate a portion of a polynucleotide bound to a substrate, and illustrates that there are several sites of the polynucleotide which may have protecting groups bound thereto, including phosphorus protecting groups (designated R in structure (VII), and sometimes referenced herein as "phosphate protecting groups"), nucleobase protecting groups (designated R" in structure (VII)); and 2'-hydroxyl protecting groups (designated R' in structure (VII), and sometimes referenced herein as 2'-O protecting groups). Note that structure (VII) only depicts two nucleotide subunits, but that typically there will be many more nucleotide subunits in the polynucleotide having the same general structure as the nucleotide subunits depicted in structure (VII). In structure (VII), B represents a nucleobase. It is contemplated that, in particular embodiments, the protecting groups (i.e. one or more of R, R', and/or R") may be labile under the same conditions that result in cleavage of the cleavable linkers (CLG in structure (VII)) described herein.

In particular embodiments the polynucleotide has a plurality of phosphate groups wherein each phosphate group is bound to a phosphate protecting group. In certain such embodiments, the phosphate protecting group is labile under the same conditions as the cleavable linker (e.g. the phosphate protecting group is peroxyanion-labile). Thus, the cleavable linker may be cleaved and the phosphate groups may undergo deprotection concurrently upon being contacted with a solution comprising an α-effect nucleophile. Any phosphate protecting group known in the art of polynucleotide synthesis that is labile under conditions of cleavage of the cleavable linker may be used. Examples of such phosphate protecting groups are described in a copending U.S. patent application filed on the same day as the instant application by Dellinger et al. entitled "Phosphorus Protecting Groups" (Ser. No. 11/388,339).

Thus, in particular embodiments, the present invention provides for a method that includes: contacting a polynucleotide bound to a substrate via a cleavable linker with a solution comprising an α-effect nucleophile; wherein the polynucleotide has a plurality of phosphate groups; wherein each phosphate group of the plurality of phosphate groups has a phosphate protecting group bound thereto, said phosphate protecting group characterized as being labile upon exposure to the α-effect nucleophile, said contacting resulting in concurrent cleavage of the polynucleotide from the substrate and deprotection of each phosphate group of the plurality of phosphate groups.

In particular embodiments the polynucleotide has a plurality of nucleobases, wherein each nucleobase is bound to a nucleobase protecting group. In certain such embodiments, the nucleobase protecting group is labile under the same conditions as the cleavable linker (e.g. the nucleobase protecting group is peroxyanion-labile). Thus, the cleavable linker may be cleaved and the nucleobases may undergo deprotection concurrently upon being contacted with a solution comprising an α-effect nucleophile. Any nucleobase protecting group known in the art of polynucleotide synthesis that is labile under conditions of cleavage of the cleavable linker may be used. Examples of such nucleobase protecting groups are described in a copending application filed on the same day as the instant application by Dellinger et al. entitled "Monomer Compositions for the Synthesis of Polynucleotides, Methods of Synthesis, and Methods of Deprotection" (Ser. No. 11/387,388).

Thus, in particular embodiments, the present invention provides for a method that includes: contacting a polynucleotide bound to a substrate via a cleavable linker with a solution comprising an α-effect nucleophile; wherein the polynucleotide has a plurality of nucleobases; wherein each nucleobase of the plurality of nucleobases has a nucleobase protecting group bound thereto, said nucleobase protecting group characterized as being labile upon exposure to the α-effect nucleophile, said contacting resulting in concurrent cleavage of the polynucleotide from the substrate and deprotection of each nucleobase of the plurality of nucleobases.

In particular embodiments the polynucleotide has a plurality of 2'-O groups wherein each 2'-O group is bound to a 2'-O protecting group (i.e. a 2'-hydroxyl protecting group). In certain such embodiments, the 2'-O protecting group is labile under the same conditions as the cleavable linker (e.g. the 2'-O protecting group is peroxyanion-labile). Thus, the cleavable linker may be cleaved and the 2'-O groups may undergo deprotection concurrently upon being contacted with a solution comprising an α-effect nucleophile. Any 2'-O protecting group known in the art of polynucleotide synthesis that is labile under conditions of cleavage of the cleavable linker may be used. Examples of such 2'-O protecting groups are described in a copending application filed on the same day as the instant application by Dellinger et al. entitled "Monomer Compositions for the Synthesis of Polynucleotides, Methods of Synthesis, and Methods of Deprotection" (Ser. No. 11/388, 112).

Thus, in particular embodiments, the present invention provides for a method that includes: contacting a polynucleotide bound to a substrate via a cleavable linker with a solution comprising an α-effect nucleophile; wherein the polynucleotide has a plurality of 2'-O groups; wherein each 2'-O group of the plurality of 2'-O groups has a 2'-O protecting group bound thereto, said 2'-O protecting group characterized as being labile upon exposure to the α-effect nucleophile, said contacting resulting in concurrent cleavage of the polynucleotide from the substrate and deprotection of each 2'-O group of the plurality of 2'-O groups.

Furthermore, in certain embodiments, the polynucleotide includes a plurality of phosphate groups, a plurality of nucleobases, and a plurality of 2'-O groups. In some embodiments, the polynucleotide also includes one or more (e.g. two or more, e.g. all three) types of protecting groups selected from phosphate protecting groups, nucleobase protecting groups, or 2'-O protecting groups. Each protecting group is bound to a corresponding site of the polynucleotide (i.e. phosphate protecting groups are bound to phosphate groups, nucleobase protecting groups are bound to nucleobases, and 2'-O protecting groups are bound to 2'-O groups). In certain embodiments, the method provides for deprotection of the polynucleotide and concurrent cleavage of the polynucleotide from the substrate. The concurrent deprotection and cleavage may include deprotection of: 1) the phosphate groups 2) the nucleobases, 3) the 2'-O groups; 4) phosphate groups and the nucleobases, 5) the nucleobases and the 2'-O groups, 6) phosphate groups and the 2'-O groups; or 7) the phosphate groups, the nucleobases, and the 2'-O groups.

In certain embodiments, the polynucleotide has a 2'-hydroxyl protecting group and at least one additional protecting group selected from a nucleobase protecting group and/or a phosphorus protecting group, wherein the 2'-hydroxyl protecting group is stable under conditions which include an α-effect nucleophile. In this regard, "stable" means that the protecting group is not susceptible to being cleaved (removed from the protected group) upon being contacted with an α-effect nucleophile. However, in these embodiments, the nucleobase protecting group and/or a phosphorus protecting group are labile under conditions which include an α-effect nucleophile; thus, the contacting with the solution of α-effect nucleophile results in concurrent cleavage of the polynucleotide from the substrate and cleavage of said nucleobase protecting groups and/or a phosphorus protecting groups. In some such embodiments, the method further provides for cleaving the 2'hydroxyl protecting group under conditions sufficient to result in cleavage of the 2'hydroxyl protecting group, wherein said conditions do not include α-effect nucleophile. The cleaving of the 2'hydroxyl protecting group in such embodiments may be either before or after the contacting with α-effect nucleophile (i.e. before or after the concurrent cleavage of the cleavable linker and nucleobase protecting group and/or a phosphorus protecting group).

In certain embodiments, the polynucleotide has a 2'-hydroxyl protecting group, a phosphorus protecting group, and a nucleobase protecting group; wherein the 2'-hydroxyl protecting group and phosphorus protecting group are stable under conditions which include an α-effect nucleophile. In these embodiments, the nucleobase protecting group is labile under conditions which include an α-effect nucleophile; thus the contacting with the solution of α-effect nucleophile results in concurrent cleavage of the polynucleotide from the substrate and cleavage of said nucleobase protecting group. In some such embodiments, the method further provides for cleaving the 2'-hydroxyl protecting group and/or the phosphorus protecting group under conditions sufficient to result in cleavage of the 2'-hydroxyl protecting group and/or the phosphorus protecting group, wherein said conditions do not include α-effect nucleophile. The cleaving of the 2'-hydroxyl protecting group and/or the phosphorus protecting group in such embodiments may be before or after the contacting with α-effect nucleophile (i.e. before or after the concurrent cleavage of the cleavable linker and nucleobase protecting group)

Experimental:

The practice of the present invention will employ, unless otherwise indicated, conventional techniques of synthetic organic chemistry, biochemistry, molecular biology, and the like, which are within the skill of the art. Such techniques are explained fully in the literature.

The present specification is put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, percents are wt./wt., temperature is in ° C. and pressure is at or near atmospheric. Standard temperature and pressure are defined as 20° C. and 1 atmosphere.

A synthesis of reagents used in certain embodiments of the present invention is now described. It will be readily apparent that the reactions described herein may be altered, e.g. by using modified starting materials to provide correspondingly modified products, and that such alteration is within ordinary skill in the art. Given the disclosure herein, one of ordinary skill will be able to practice variations that are encompassed by the description herein without undue experimentation.

Synthesis of 5'-O-Dimethoxytrityl-2'-O-tert-butylthiocarbonate-3'-O-(4-nitrophenyl)carbonate uridine

5'-O-Dimethoxytrityl-2'-O-tert-butylthiocarbonate uridine (0.5 mmole) was coevaporated 3 times with pyridine, and then dried on vacuum pump for 2 hours. Anhydrous pyridine (5 mL) and 4-nitrophenyl chloroformate (153 mg, 0.75 mmole) were added, and the mixture was stirred at room temperature for 16 hours. Product was purified by flash chromatography using hexanes:Py (99.9:0.1) with a gradient of ethyl acetate (0-40%). The yield was 46%.

Preparation of TENTA GEL Solid Support with Thiocarbonate Linker

TENTA GEL thio resin (1 g) (Rapp Polymere GmbH, Tubingen, Germany) and 5'-O-Dimethoxytrityl-2'-O-tert-butylthiocarbonate-3'-O-(4-nitrophenyl)carbonate uridine (148 mg, 0.7 eq) were dried separately on vacuum pump for 12 hours. Anhydrous 1,4-dioxane (5 mL) was added to TENTA GEL resin and left for 20 min. After that time 1,8-diazabicyclo[5.4.0]undec-7-ene (0.041 mL, 1.1 eq) was added and the mixture was shaken for about 5 min. Solution of 5'-O-dimethoxytrityl-2'-O-tert-butylthiocarbonate-3'-O-(4-nitrophenyl)carbonate uridine in anhydrous 1,4-dioxane (2 mL) was then added. The flask was tightly capped and shaken for 3 days. Solid support was filtered off and washed successively with dioxane, methanol, and DCM, and then dried on vacuum pump. The loading of the obtained solid support was 28.3 micromole/g.

The result is a single nucleoside moiety bound to the substrate via a cleavable linker; wherein the cleavable linker has the structure (I) as described above. The single nucleoside moiety has a 5'-hydroxyl protecting group. Removal of the 5'-hydroxyl protecting group provides an initial hydroxyl to which a nucleoside phosphoramidite may be coupled in the first step of a standard polynucleotide synthesis method. Synthesis of a polynucleotide may be performed, and the synthesized polynucleotide will be attached to the substrate via the cleavable linker.

Synthesis of a (dT)$_8$ polynucleotide was performed on a TENTA GEL solid support with a cleavable linker, giving the following product:

(wherein the solid circle represents the TENTA GEL).

Figure 1:
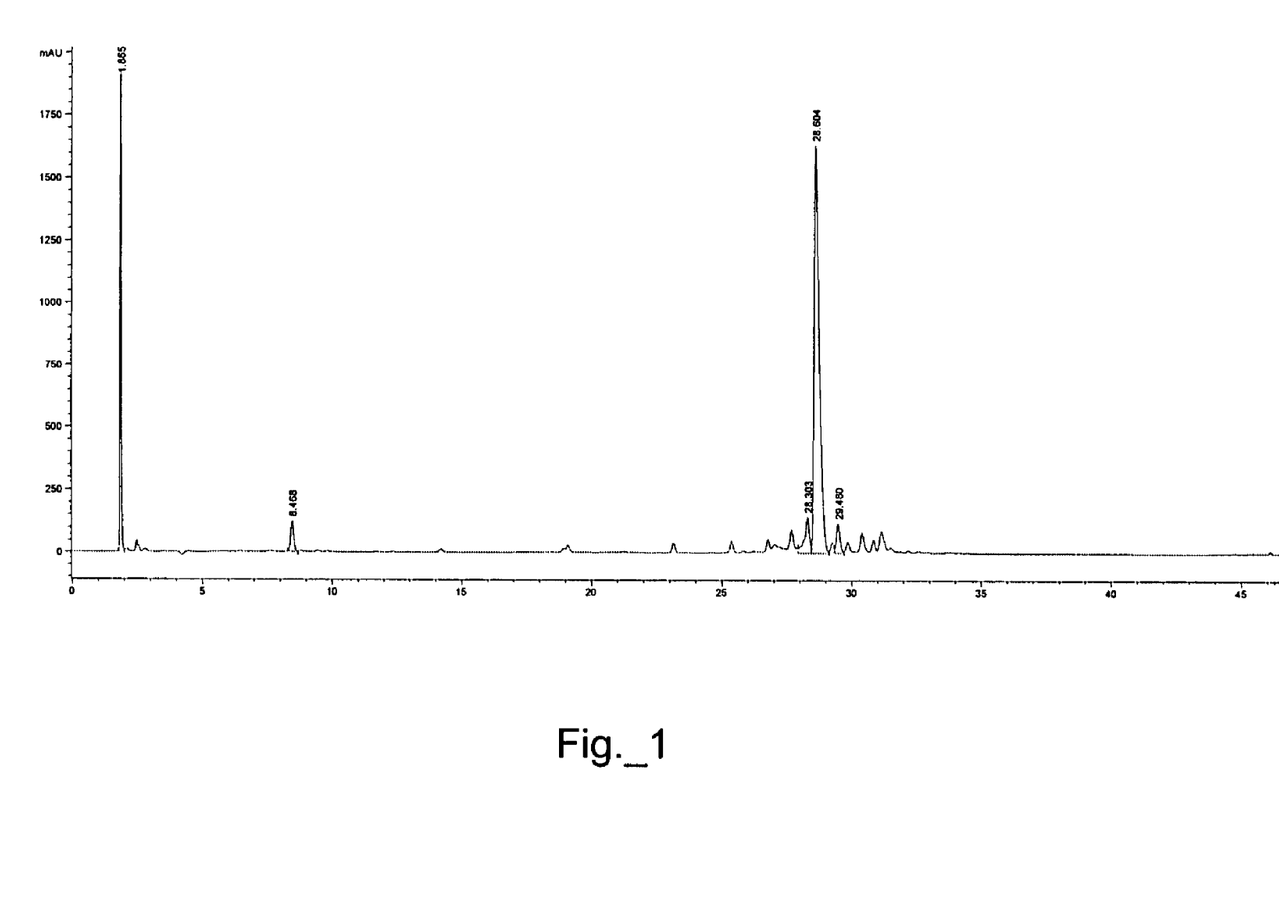
FIG. 1 is a chromatogram of a polynucleotide cleaved from a substrate in an embodiment of the present invention.

The product was then contacted with 5% hydrogen peroxide (pH 9.4, 50 mM alkaline buffer, 10% methanol) for approximately 30 minutes. The crude cleavage mixture was analysed using reverse phase-HPLC on a HYPERSYL column (Hypersil, Holliston, Mass.), eluted with TEAAc/acetonitrile. FIG. 1 shows the chromatogram obtained.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method comprising:
    contacting a synthetic polynucleotide that is covalently bound at a terminal nucleotide of the synthetic polynucleotide to a substrate via a cleavable linker with a solution comprising an α-effect nucleophile to result in cleavage of the synthetic polynucleotide from the substrate;
    wherein the cleavable linker has the structure (I):

wherein:
    Lnk is a linking group;
    Sub denotes the site at which the substrate is attached to the cleavable linker; and
    RPN is a 2'-, 3'- or 5'-position of the terminal nucleotide of the synthetic polynucleotide; and
    wherein the cleaved synthetic polynucleotide comprises a hydroxyl group at the 2'-, 3'- or 5'-position of the terminal nucleotide.

2. The method of claim 1 wherein the solution is at a pH of about 6 to about 12.

3. The method of claim 1 wherein the α-effect nucleophile is characterized as having a pKa in the range of about 4 to 13.

4. The method of claim 1 wherein the solution comprising the α-effect nucleophile is a solution comprising one or more species selected from hydrogen peroxide, a peracid, a perboric acid, an alkylperoxide, a hydroperoxide, a butylhydroperoxide, a benzylhydroperoxide, a phenylhydroperoxide, a cumene hydroperoxide, performic acid, a peracetic acid, perbenzoic acid, a substituted perbenzoic acid, chloroperbenzoic acid, perbutyric acid, tertiary-butylperoxybenzoic acid, decanediperoxoic acid, corresponding salts of said species, and combinations thereof.

5. The method of claim 1 wherein the solution comprising the α-effect nucleophile is a solution comprising one or more species selected from hydrogen peroxide, salts of hydrogen peroxide, and mixtures of hydrogen peroxide and performic acid.

6. The method of claim 1 wherein the α-effect nucleophile is formed in situ by a reaction of hydrogen peroxide and a carboxylic acid or carboxylic acid salt.

7. The method of claim 1, wherein the linking group Lnk is selected from:
    (1) a lower alkyl group;
    (2) a modified lower alkyl group in which one or more linkages selected from ether-, thio-, amino-, oxo-, ester-, and amido- is present;
    (3) a modified lower alkyl substituted with one or more groups including lower alkyl; aryl, aralkyl, alkoxyl, thioalkyl, hydroxyl, amino, amido, sulfonyl, halo; or
    (4) a modified lower alkyl substituted with one or more groups including lower alkyl; alkoxyl, thioalkyl, hydroxyl, amino, amido, sulfonyl, halo, and in which one or more linkages selected from ether-, thio-, amino-, oxo-, ester-, and amido- is present.

8. The method of claim 1, wherein the linking group Lnk has the structure

—(CH2)$_m$-Lkg-(CH2)$_n$- wherein:
m and n are integers independently selected from the range of 1 to about 12, and
Lkg is a linkage selected from ether-, thio-, amino-, oxo-, ester-, or amido-.

9. The method of claim 1, further comprising recovering the polynucleotide after cleavage of the synthetic polynucleotide from the substrate.

10. The method of claim 1, wherein the synthetic polynucleotide comprises at least one protecting group selected from a nucleobase protecting group, a 2'-hydroxyl protecting group, and a phosphate protecting group, wherein said at least one protecting group is labile under conditions which include an α-effect nucleophile; and wherein said contacting results in concurrent cleavage of the synthetic polynucleotide from the substrate and deprotection of the synthetic polynucleotide.

11. The method of claim 1:
wherein the synthetic polynucleotide that is covalently bound at a terminal nucleotide of the synthetic polynucleotide to a substrate via the cleavable linker is an RNA, said RNA has a 2'-hydroxyl protecting group, said 2'hydroxyl protecting group is characterized as being peroxyanion-labile;
wherein the α-effect nucleophile is a peroxyanion; and
wherein said contacting results in concurrent cleavage of the RNA from the substrate and cleavage of the 2'-hydroxyl protecting group.

12. The method of claim 1:
wherein the synthetic polynucleotide comprises a 2'-hydroxyl protecting group and at least one additional protecting group selected from a nucleobase protecting group and a phosphorus protecting group;
wherein said 2'-hydroxyl protecting group is stable under conditions which include an α-effect nucleophile;
wherein said at least one additional protecting group is labile under conditions which include an α-effect nucleophile; and
wherein said contacting results in concurrent cleavage of the synthetic polynucleotide from the substrate and cleavage of said at least one additional protecting group.

13. The method of claim 12 further comprising cleaving the 2'hydroxyl protecting group under conditions sufficient to result in cleavage of the 2'hydroxyl protecting group, wherein said conditions do not include α-effect nucleophile.

14. The method of claim 1, further comprising:
prior to said contacting:
synthesizing said synthetic polynucleotide by a sequential addition of nucleotide monomers to a nucleotide or nucleoside monomer that is covalently bound to said substrate via said cleavable linker.

* * * * *

UNITED STATES PATENT AND TRADEMARK OFFICE
CERTIFICATE OF CORRECTION

| | | |
|---|---|---|
| PATENT NO. | : 7,855,281 B2 | Page 1 of 1 |
| APPLICATION NO. | : 11/389326 | |
| DATED | : December 21, 2010 | |
| INVENTOR(S) | : Douglas J. Dellinger et al. | |

It is certified that error appears in the above-identified patent and that said Letters Patent is hereby corrected as shown below:

In column 20, line 9, in Claim 1, delete "the" and insert -- said --, therefor.

Signed and Sealed this
Fourteenth Day of August, 2012

David J. Kappos
*Director of the United States Patent and Trademark Office*